United States Patent
Gante et al.

[11] 3,975,403
[45] Aug. 17, 1976

[54] SULFUR-CONTAINING RING COMPOUNDS

[75] Inventors: Joachim Gante; Werner Mehrhof; Albrecht Wild, all of Darmstadt, Germany

[73] Assignee: Merck Patent Gesellschaft mit beschrankter Haftung, Darmstadt, Germany

[22] Filed: Sept. 10, 1973

[21] Appl. No.: 395,980

[30] Foreign Application Priority Data
Sept. 19, 1972 Germany............................ 2245940

[52] U.S. Cl. ............................. 260/327 P; 424/275; 424/276; 424/277; 260/328

[51] Int. Cl.² ............... C07D 327/08; C07D 335/12; C07D 339/08

[58] Field of Search ..................... 260/327 P, 328

[56] References Cited
UNITED STATES PATENTS
3,639,612  2/1972  DeLong, et al. ................... 424/276

OTHER PUBLICATIONS
Vasiliu, et al., C.A. 60: 14499–14500, (1962).

Maior, C.A. 68: 12922u, (1968).

Paget, et al., C.A. 73: 64571b, (1970).

*Primary Examiner*—John D. Randolph
*Attorney, Agent, or Firm*—Millen, Raptes & White

[57] ABSTRACT

Compounds of the formula

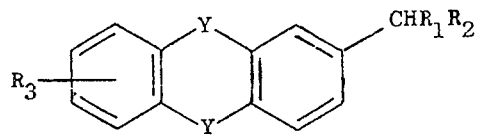

wherein $R_1$ is COOH, COO-alkyl, $CH_2OH$ or $CH_2$-alkanoyl; $R_2$ is $CH_3$ or $C_2H_5$; $R_3$ is H, F, Cl or Br; and Y is $CH_2$, O or S, at least one Y being S, and the physiologically acceptable salts thereof, possesses antiphlogistic activity.

25 Claims, No Drawings

SULFUR-CONTAINING RING COMPOUNDS

BACKGROUND OF THE INVENTION

This invention relates to novel sulfur-containing ring compounds. Compounds similar to the novel compounds of this invention are known but are less effective. See Chem. Abstracts 44, 2559 (1950); 55, 23542 (1961).

SUMMARY OF THE INVENTION

The sulfur-containing ring compounds of this invention are compounds of the general formula $$Z-CHR_1R_2 \qquad I$$

wherein Z is

in which $R_1$ is COOH, COOR$_4$, CH$_2$OH or CH$_2$OR$_5$; $R_2$ is CH$_3$ or C$_2$H$_5$; $R_3$ is H, F, Cl or Br; $R_4$ is alkyl of 1–8 carbon atoms; $R_5$ is alkanoyl of 2–4 carbon atoms; and Y is CH$_2$, O or S, at least one Y being S, and the physiologically acceptable salts thereof.

DETAILED DISCUSSION

The compounds of Formula I possess, with good compatibility, excellent antiphlogistic effects, i.e., anti-inflammatory activity, especially systemic. For example, they have a favorable influence on the chronically progressing disease processes of the joints. They also exhibit analgesic and antipyretic activity. The compounds of Formula I can thus be employed as pharmaceutical drugs, especially for obtaining antiphlogistic effects in living beings. They are also useful as intermediates for the preparation of other drugs.

Preferred compounds of Formula I include the especially preferred thianthrenes of Formula Ia, the thioxanthenes of Formulae Ib and Ic, and the phenoxathiins of Formula Id and Ie:

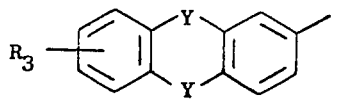

Ia

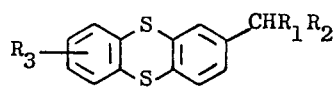

Ib

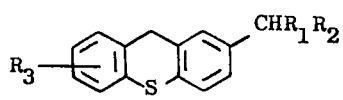

Ic

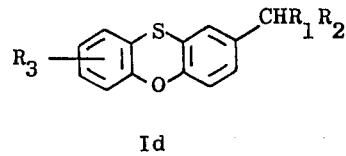

Id

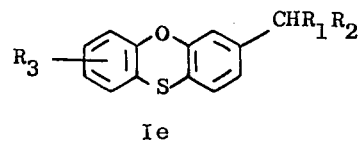

Ie

Of the thioxanthenes, those of Formula Ib are preferred, and of the phenoxathiins, those of Formula Id are preferred.

In the above formulae, including Formula I:

a. $R_1$ is preferably COOH, especially COOCH$_3$, COOC$_2$H$_5$, CH$_2$OH, or CH$_2$OCOCH$_3$;

b. $R_2$ is preferably CH$_3$;

c. $R_3$ is preferably H, and when other than H, preferably is positioned "meta," i.e., in the 7- or 8-position of compounds of Formulae Ia, Id and Ie, and in the 6- or 7-position of compounds of Formulae Ib and Ic;

d. $R_4$ is preferably methyl or ethyl but can also be, e.g., n-propyl, isopropyl, n-butyl, isobutyl, sec.-butyl, tert.-butyl, n-pentyl, isoamyl, n-hexyl, n-heptyl, n-octyl, 2-ethyl-hexyl; and e. $R_5$ is preferably acetyl but can also be propionyl, butyryl or isobutyryl.

The numbering of the individual positions of the above formulae is in accordance with the disclosure in "The Ring Index," Second Edition, 1960 (Nos. 3449, 3607 and 3408).

In the process aspect of this invention, compounds of Formula I are prepared in accordance with conventional methods in a compound of the general formula Z—X (II) wherein X is a group convertible into the —CHR$_1$R$_2$ group of Formula I and Z, R$_1$, R$_2$, R$_3$ and Y have the values given for Formula I, by converting X into the group —CHR$_1$R$_2$. Optionally thereafter, a thus-obtained compound of Formula I can be converted in one or several steps into a different compound of Formula I by converting one or both of R$_1$ and/or R$_3$ into another R$_1$ and/or R$_3$ group, respectively. X is preferably a group which can be reduced to the group —CHR$_1$R$_2$, especially —CR$_1$=CH$_2$, —CR$_1$=CHCH$_3$ or —CR$_1$R$_2$—OH, or a group which can be solvolyzed, especially hydrolyzed, to the group —CHR$_1$R$_2$, primarily —CHR$_2$—CN.

The following is a preferred method for producing compounds of Formula I:

A thianthrene or thioxanthene or phenoxathiin derivative, respectively, of the formula Z—H is reacted by a Friedel-Crafts reaction with ethoxalyl chloride to the corresponding glyoxylic acid ethyl ester of the formula Z—CO—COOC$_2$H$_5$, which is converted, by reaction with an organometallic compound of the formula R$_2$M, into the corresponding tertiary hydroxy ester of the formula Z—CR$_2$(OH)—COOC$_2$H$_5$, which ester is reducible, e.g., with tin (II) chloride, to the desired ester Z—CHR$_2$—COOC$_2$H$_5$. By hydrolysis, the corresponding carboxylic acid of the formula Z—CHR$_2$COOH is obtained, which can be converted into an ester of the formula Z—CHR$_2$—COOR$_4$ by esterification with an alcohol of the formula R$_4$OH, for example, in the presence of a mineral acid. Reduction of these esters and acids, for example with LiAlH$_4$, yields the corresponding alcohols of the formula Z—CHR$_2$—CH$_2$OH which, by acylation with chlorides or anhydridesof the carboxylic acids of the formula R$_5$OH produces acylates of the formula Z—CHR$_2$—CH$_2$OR$_5$.

The free carboxylic acids of Formula I (R$_1$ = COOH) can be converted, by reaction with a base, into physiologically acceptable metallic and/or ammonium salts thereof. Especially suitable salts are the sodium, potassium, magnesium, calcium and ammonium salts, and substituted ammonium salts, such as, for example, dialkylamine, e.g., dimethyl- and diethylammonium salts and the corresponding alkanolamine salts, e.g., monoethanol-, diethanol- and triethanolammonium, and the cycloalkylammonium, e.g., cyclohexylammonium and dicyclohexylammonium, salts.

Conversely, the free carboxylic acids can be obtained from the acid addition salts thereof by treatment with strong bases, e.g., sodium or potassium hydroxide, sodium or potassium carbonate.

When the compounds of Formula I contain an asymmetrical carbon atom, they are ordinarily obtained in the racemic form. Those racemates can be separated into the optical antipodes thereof in accordance with methods known in the literature. Chemical separation is preferred. According to this process, diastereomers are formed from the racemic mixture by reaction with an optically active auxiliary agent. For example, diastereomeric salts of the compounds of Formula I (R$_1$ = COOH) can be reacted with optically active amines, such as quinine, cinchonidine, brucine, cinchonine, hydroxyhydrindamine, morphine, 1-phenylethylamine, 1-naphthylethylamine, phenyloxynaphthylmethylamine, quinidine, strychnine, basic amino acids, such as lysine, arginine. By hydrolytic dissociation of the thereafter isolated diastereomeric compound, the desired optically acitive compound of Formula I is obtained. It is, of course, also possible to obtain optically active compounds in accordance with the described methods by the use of optically active starting compound.

The compounds of Formula I and/or optionally the physiologically acceptable salts thereof can be employed in a mixture with solid, liquid and/or semiliquid excipients as drugs in the human or veterinary medicine. Suitable vehicles are those organic or inorganic substances amenable to parenteral, enteral or topical application and which do not react with the novel compounds, such as, for example, water, vegetable oils, benzyl alcohols, polyethylene glycols, gelatin, lactose, amylose, magnesium stearate, talc, vaseline, cholesterol. Especially suitable for parenteral application are solutions, preferably oily or aqueous solutions, as well as suspensions, emulsions or implants. Suitable for enteral administration are tablets, dragees, capsules, syrups, elixirs or suppositories, and for topical application, salves, creams and powders. The above-described preparations can optionally be sterilized or can contain auxiliary substances, such as lubricants, preservatives, stabilizers or wetting agents, emulsifiers, salts for influencing the osmotic pressure, buffers, coloring, flavoring and/or aromatous substances.

The compounds are preferably administered in dosages of between 1 and 500 mg. per dosage unit, the exact dosage depending, e.g., upon the mode of administration, the activity of the selected compound and the patient's response.

The temperatures herein are indicated in degrees Celsius. "Worked up as usual" means that, if necessary, water is added; the mixture is extracted with ethyl acetate, ether or chloroform; separated; the organic extract is washed with water, dried over sodium sulfate, filtered and the solvent is distilled off; and the residue distilled and/or crystallized. THF = tetrahydrofuran.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE a. 33 g. of the ethyl ester of 2-(2-thianthrenyl)-2-hydroxypropionic acid (obtainable by reacting thianthrene with ethoxalyl chloride in 1,2-dichloroethane in the presence of AlCl$_3$ at 10°–20° and reacting the thus-obtained ethyl ester of 2-thianthrenylglyoxylic acid (m.p. 68°–69°) with CH$_3$MgI in ether) is dissolved in 500 ml. of xylene; 1 g. of p-toluenesulfonic acid is added thereto, and the mixture is refluxed for 3½ hours with the use of a water trap. After cooling, the reaction mixture is washed with sodium bicarbonate solution and water, separated, dried over sodium sulfate, and evaporated. The thus-produced oily ethyl ester of 2-(2-thianthrenyl)-acrylic acid is dissolved in 270 ml. of ethanol and hydrogenated on 8 g. of 4% palladium charcoal at 50° and under 6 atmospheres until the hydrogen absorption is terminated (3 hours). The product is filtered, concentrated by evaporation, and the ethyl ester of 2-(2-thianthrenyl)-propionic acid is thus obtained, b.p. 225°–229°/0.2 mm.

Analogously, with the use of the following compounds:

ethyl ester of 2-(2-thioxanthenyl)-acrylic acid [obtainable from thioxanthene by way of the ethyl ester of 2-thioxanthenylglyoxylic acid and the ethyl ester of 2-(2-thioxanthenyl)-2-hydroxypropionic acid];
ethyl ester of 2-(2-phenoxathiinyl)-acrylic acid;
ethyl ester of 2-(7-fluoro-2-thianthrenyl)-acrylic acid;
ethyl ester of 2-(8-fluoro-2-thianthrenyl)-acrylic acid [obtainable, in addition to the above-mentioned isomer, from 2-fluorothianthrene by way of the ethyl ester of 7- or 8-fluoro-2-thianthrenyl-glyoxylic acid and the ethyl ester of 2-(7- or 2-(8-fluoro-2-thianthrenyl)-2-hydroxypropionic acid];
ethyl ester of 2-(7-chloro-2-thianthrenyl)-acrylic acid;
ethyl ester of 2-(8-chloro-2-thianthrenyl)-acrylic acid;
ethyl ester of 2-(7-bromo-2-thianthrenyl)-acrylic acid;
ethyl ester of 2-(8-bromo-2-thianthrenyl)-acrylic acid;
ethyl ester of 2-(7-fluoro-2-thioxanthenyl)-acrylic acid;
ethyl ester of 2-(7-chloro-2-thioxanthenyl)-acrylic acid (obtainable from 2-chlorothioxanthene);
ethyl ester of 2-(7-bromo-2-thioxanthenyl)-acrylic acid;
ethyl ester of 2-(8-fluoro-2-phenoxathiinyl)-acrylic acid;
ethyl ester of 2-(8-chloro-2-phenoxathiinyl)-acrylic acid;

ethyl ester of 2-(8-bromo-2-phenoxathiinyl)-acrylic acid [obtainable from 2-bromophenoxathiin by way of the ethyl ester of 8-bromo-2-phenoxathiinyl-glyoxylic acid (m.p. 97°–99°) and the ethyl ester of 2-(8-bromo-2-phenoxathiinyl)-2-hydroxypropionic acid];
ethyl ester of 2-(2-thianthrenyl)-crotonic acid;
ethyl ester of 2-(2-thioxanthenyl)-crotonic acid;
ethyl ester of 2-(2-phenoxathiinyl)-crotonic acid, the final compounds set forth below can be produced by hydrogenation:

ethyl ester of 2-(2-thioxanthenyl)-propionic acid;
ethyl ester of 2-(2-phenoxathiinyl)-propionic acid;
ethyl ester of 2-(7-fluoro-2-thianthrenyl)-propionic acid;
ethyl ester of 2-(8-fluoro-2-thianthrenyl)-propionic acid;
ethyl ester of 2(7-chloro-2-thianthrenyl)-propionic acid;
ethyl ester of 2-(8-chloro-2-thianthrenyl)-propionic acid;
ethyl ester of 2-(7-bromo-2-thianthrenyl)-propionic acid;
ethyl ester of 2-(8-bromo-2-thianthrenyl)-propionic acid;
ethyl ester of 2-(7-fluoro-2-thioxanthenyl)-propionic acid;
ethyl ester of 2-(7-chloro-2-thioxanthenyl)-propionic acid;
ethyl ester of 2-(7-bromo-2-thioxanthenyl)-propionic acid;
ethyl ester of 2-(8-fluoro-2-phenoxathiinyl)-propionic acid;
ethyl ester of 2-(8-chloro-2-phenoxathiinyl)-propionic acid;
ethyl ester of 2-(8-bromo-2-phenoxathiinyl)-propionic acid;
ethyl ester of 2-(2-thianthrenyl)-butyric acid;
ethyl ester of 2-(2-thioxanthenyl)-butyric acid;
ethyl ester of 2-(2-phenoxathiinyl)-butyric acid.

b. 31.6 g. of the ethyl ester of 2-(2-thianthrenyl)-propionic acid is refluxed with 10 g. of KOH in 250 ml. of ethanol for 2 hours. The reaction mixture is evaporated, the residue dissolved with water, washed with ether, acidified with hydrochloric acid to a pH of 3, and worked up as usual, thus obtaining 2-(2-thianthrenyl)-propionic acid, m.p. 130°–132°. Na salt, m.p. 205°–210°. Cyclohexylammonium salt, m.p. 226°–229°. 4-Carbethoxycyclohexylammonium salt, m.p. 180°–182°.

In place of KOH, it is also possible to utilize equivalent amounts of NaOH, Na₂CO₃, or K₂CO₃.

Analogously, by saponification of the corresponding esters, the following compounds are produced:

2-(2-thioxanthenyl)-propionic acid, m.p. 170°–172°;
2-(2-phenoxathiinyl)-propionic acid, m.p. 116°–118°;
2-(7-fluoro-2-thianthrenyl)-propionic acid;
2-(8-fluoro-2-thianthrenyl)-propionic acid;
2-(7-chloro-2-thianthrenyl)-propionic acid;
2-(8-chloro-2-thianthrenyl)-propionic acid;
2-(7-bromo-2-thianthrenyl)-propionic acid;
2-(8-bromo-2-thianthrenyl)-propionic acid;
2-(7-fluoro-2-thioxanthenyl)-propionic acid;
2-(7-chloro-2-thioxanthenyl)-propionic acid, m.p. 140°–145°;
2-(7-bromo-2-thioxanthenyl)-propionic acid;
2-(8-fluoro-2-phenoxathiinyl)-propionic acid;
2-(8-chloro-2-phenoxathiinyl)-propionic acid;
2-(8-bromo-2-phenoxathiinyl)-propionic acid, m.p. 153°–155°;
2-(2-thianthrenyl)-butyric acid, m.p. 160°–162°;
2-(2-thioxanthenyl)-butyric acid;
2-(2-phenoxathiinyl)-butyric acid.

c. One gram of 2-(2-thianthrenyl)-propionic acid is allowed to stand in 15 ml. of methanolic hydrochloric acid for 24 hours at room temperature. The reaction mixture is then evaporated, worked up as usual, and the product is the methyl ester of 2-(2-thianthrenyl)-propionic acid, b.p. 210°–215°/0.2 mm.

In an analogous mode of operation (reaction times of up to 3 days), one obtains from the corresponding acids, by reaction with HCl in methanol, ethanol, n-propanol, isopropanol, n-butanol, isobutanol, sec.-butanol, n-pentanol, isopentanol, n-hexanol, n-heptanol, n-octanol, and 2-ethylhexanol, respectively, the corresponding methyl, ethyl, n-propyl, isopropyl, n-butyl, isobutyl, sec.-butyl, n-pentyl, isopentyl, n-hexyl, n-heptyl, n-octyl, and 2-ethylhexyl esters, respectively, for example the ethyl ester (b.p. 225°–229°/0.2 mm.), n-propyl ester, isopropyl ester, n-butyl ester, isobutyl ester, sec.-butyl ester, n-pentyl ester, isopentyl ester, n-hexyl ester, n-heptyl ester, n-octyl ester, and 2-ethylhexyl ester of 2-(2-thianthrenyl)-propionic acid; as well as the methyl ester, ethyl ester, n-propyl ester, isopropyl ester, n-butyl ester, isobutyl ester, sec.-butyl ester, n-pentyl ester, isopentyl ester, n-hexyl ester, n-heptyl ester, n-octyl ester, and 2-ethylhexyl ester of 2-(2-thioxanthenyl)-propionic acid; as well as the methyl ester, ethyl ester (b.p. 175°–180°/0.4 mm.), n-propyl ester, isopropyl ester, n-butyl ester, isobutyl ester, sec.-butyl ester, n-pentyl ester, isopentyl ester, n-hexyl ester, n-hepthyl ester, n-octyl ester, and 2-ethylhexyl ester of 2-(2-phenoxathiinyl)-propionic acid.

d. A solution of 31.6 g. of the ethyl ester of 2-(2-thianthrenyl)-propionic acid in 250 ml. of absolute THF is added dropwise to a suspension of 3.8 g. of LiAlH₄ in 150 ml. of THF. The mixture is stirred for 30 minutes, and then a mixture of 20 ml. of THF, 5 ml. of water, and 10 ml. of 32% sodium hydroxide solution is added thereto dropwise under ice cooling. The mixture is then filtered over kieselguhr, dried, evaporated, and the product thus obtained is 2-(2-thianthrenyl)-propanol, b.p. 212°–215°/0.05 mm.

Analogously, the following products are obtained by reduction of the corresponding esters with LiAlH₄:

2-(2-thioxanthenyl)-propanol, m.p. 74°–77°
2-(2-phenoxathiinyl)-propanol, b.p. 190°–192°/0.15 mm.
2-(7-fluoro-2-thianthrenyl)-propanol
2-(8-fluoro-2-thianthrenyl)-propanol
2-(7-chloro-2-thianthrenyl)-propanol
2-(8-chloro-2-thianthrenyl)-propanol
2-(7-bromo-2-thianthrenyl)-propanol
2-(8-bromo-2-thianthrenyl)-propanol
2-(7-fluoro-2-thioxanthenyl)-propanol
2-(7-chloro-2-thioxanthenyl)-propanol
2-(7-bromo-2-thioxanthenyl)-propanol
2-(8-fluoro-2-phenoxathiinyl)-propanol
2-(8-chloro-2-phenoxathiinyl)-propanol 2-(8-bromo-2-phenoxathiinyl)-propanol
2-(2-thianthrenyl-1-butanol
2-(2-thioxanthenyl)-1-butanol
2-(2-phenoxathiinyl)-1-butanol.

e. One gram of 2-(2-thianthrenyl)-propanol is allowed to stand in 5 ml. of pyridine and 5 ml. of acetic anhydride for 24 hours. The mixture is then concentrated, worked up as usual, and the product is 2-(2-thianthrenyl)-propyl acetate, b.p. 232°–234°/0.1 mm.

Analogously, the corresponding acetates are obtained from the corresponding alcohols, for example:

2-(2-thioxanthenyl)-propyl acetate, b.p. 208°–211°/0.2 mm.
2-(2-phenoxathiinyl)-propyl acetate, b.p. 196°–197°/0.1 mm.
2-(7-fluoro-2-thianthrenyl)-propyl acetate
2-(8-flouro-2-thianthrenyl)-propyl acetate
2-(7-chloro-2-thianthrenyl)-propyl acetate
2-(8-chloro-2-thianthrenyl)-propyl acetate
2-(7-bromo-2-thianthrenyl)-propyl acetate
2-(8-bromo-2-thianthrenyl)-propyl acetate
2-(7-fluoro-2-thioxanthenyl)-propyl acetate
2-(7-chloro-2-thioxanthenyl)-propyl acetate
2-(7-bromo-2-thioxanthenyl)-propyl acetate
2-(8-fluoro-2-phenoxathiinyl)-propyl acetate
2-(8-chloro-2-phenoxathiinyl)-propyl acetate
2-(8-bromo-2-phenoxathiinyl)-propyl acetate
2-(2-thianthrenyl)-1-butyl acetate
2-(2-thioxanthenyl)-1-butyl acetate
2-(2-phenoxathiinyl)-1-butyl acetate.

With the aid of propionic acid anhydride and/or butyric acid anhydride, the corresponding propionates and/or butyrates are analogously produced, for example:

2-(2-thianthrenyl)-propyl propionate
2-(2-thioxanthenyl)-propyl propionate
2-(2-phenoxathiinyl)-propyl propionate
2-(2-thianthrenyl)-propyl butyrate
2-(2-thioxanthenyl)-propyl butyrate
2-(2-phenoxathiinyl)-propyl butyrate.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A compound of the formula

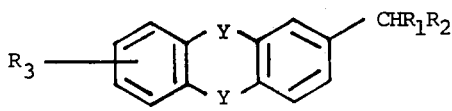

wherein $R_1$ is COOH, COOR$_4$; $R_2$ is $CH_3$ or $C_2H_5$; $R_3$ is H, F, Cl or Br; $R_4$ is alkyl of 1–8 carbon atoms; and Y is $CH_2$, O or S, at least one Y being S; and the physiologically acceptable salts thereof.

2. A compound of the formula

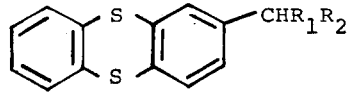

wherein $R_1$ is $CH_2OH$ or $CH_2OR_5$; $R_2$ is $CH_3$ or $C_2H_5$; $R_3$ is H, F, Cl or Br; $R_5$ is alkanoyl of 2–4 carbon atoms; and the physiologically acceptable salts thereof.

3. A compound of the formula

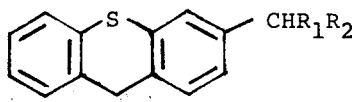

wherein $R_1$ is $CH_2OH$ or $CH_2OR_5$; $R_2$ is $CH_3$ or $C_2H_5$; $R_3$ is H, F, Cl or Br; $R_5$ is alkanoyl of 2–4 carbon atoms; and the physiologically acceptable salts thereof.

4. A compound of claim 1 wherein $R_1$ is COOH.
5. A compound of claim 1 wherein $R_1$ is COOR$_4$.
6. A compound of claim 1 wherein $R_2$ is $CH_3$.
7. A compound of claim 1 wherein both Y are S.
8. A compound of claim 1 wherein one Y is $CH_2$ and the other is S.
9. A compound of claim 1 wherein one Y is O and the other is S.
10. The compound of claim 1, 2-(2-thianthrenyl)-propionic acid.
11. The compound of claim 1, methyl ester of 2-(2-thianthrenyl)-propionic acid.
12. The compound of claim 1, ethyl ester of 2-(2-thianthrenyl)-propionic acid.
13. The compound of claim 1, n-butyl ester of 2-(2-thianthrenyl)-propionic acid.
14. The compound of claim 1, 2-(2-thianthrenyl)-butyric acid.
15. The compound of claim 2, 2-(2-thianthrenyl)-propanol.
16. The compound of claim 2, 2-(2-thianthrenyl)-propyl acetate.
17. The compound of claim 1, 2-(2-thioxanthenyl)-propionic acid.
18. The compound of claim 1, 2-(2-thioxanthenyl)-propionic acid ethyl ester.
19. The compound of claim 1, 2(7-chloro-2-thioxanthenyl)-propionic acid.
20. The compound of claim 3, 2-(2-thioxanthenyl)-propanol.
21. The compound of claim 3, 2-(2-thioxanthenyl)-propyl acetate.
22. The compound of claim 1, 2-(2-phenoxathiinyl)-propionic acid.
23. The compound of claim 1, 2-(2-phenoxathiinyl)-propionic acid ethyl ester.
24. The compound of claim 1, 2-(8-bromo-2-phenoxathiinyl)-propionic acid.
25. A compound of claim 1 wherein $R_1$ is $CH_2OR_5$.

UNITED STATES PATENT OFFICE
CERTIFICATE OF CORRECTION

PATENT NO. : 3,975,403
DATED : August 17, 1976
INVENTOR(S) : Joachim GANTE et al It is certified that error appears in the above-identified patent and that said Letters Patent are hereby corrected as shown below:

Claim 2, line 2: Formula should read as follows:

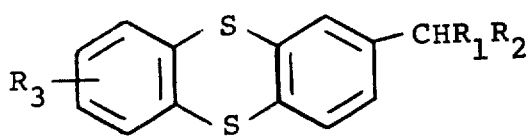

Claim 3, line 2: Formula should read as follows:

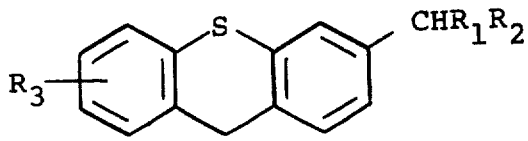

Signed and Sealed this

Twenty-third Day of November 1976

[SEAL]

Attest:

RUTH C. MASON
*Attesting Officer*

C. MARSHALL DANN
*Commissioner of Patents and Trademarks*